US008349368B2

(12) United States Patent
Gordon et al.

(10) Patent No.: US 8,349,368 B2
(45) Date of Patent: Jan. 8, 2013

(54) COMPOSITIONS AND METHODS FOR TREATING VAGINAL INFECTIONS AND PATHOGENIC VAGINAL BIOFILMS

(75) Inventors: Suzanne Gordon, Chicago, IL (US); Dawn Flynn, Elmhurst, IL (US)

(73) Assignee: Toltec Pharmaceuticals, LLC, Chicago, IL (US)

( * ) Notice: Subject to any disclaimer, the term of this patent is extended or adjusted under 35 U.S.C. 154(b) by 615 days.

(21) Appl. No.: 12/323,585

(22) Filed: Nov. 26, 2008

(65) Prior Publication Data

US 2009/0181106 A1    Jul. 16, 2009

Related U.S. Application Data

(60) Provisional application No. 60/991,308, filed on Nov. 30, 2007.

(51) Int. Cl.
*A61K 33/22* (2006.01)
*A61K 31/132* (2006.01)
*A01N 59/14* (2006.01)
*A01N 33/04* (2006.01)

(52) U.S. Cl. ........................................ 424/659; 514/667

(58) Field of Classification Search ........................ None
See application file for complete search history.

(56) References Cited

U.S. PATENT DOCUMENTS

| | | | |
|---|---|---|---|
| 4,107,331 A | | 8/1978 | Rosenberg |
| 4,551,456 A | * | 11/1985 | Katz ........................ 514/253.08 |
| 5,853,767 A | | 12/1998 | Melman |
| 6,106,854 A | | 8/2000 | Belfer et al. |
| 6,420,425 B1 | | 7/2002 | Melman |
| 6,762,160 B2 | | 7/2004 | Barbeau et al. |
| 7,074,776 B2 | | 7/2006 | Cooper et al. |
| 2003/0216479 A1 | * | 11/2003 | Huang et al. .................. 514/721 |
| 2005/0148570 A1 | | 7/2005 | Huang et al. |
| 2005/0222169 A1 | * | 10/2005 | Ahmad et al. ........... 514/254.07 |
| 2006/0276339 A1 | | 12/2006 | Windsor et al. |
| 2007/0231406 A1 | | 10/2007 | Bucalo et al. |

FOREIGN PATENT DOCUMENTS

| | | |
|---|---|---|
| EP | 1 312 380 A1 | 5/2003 |
| GR | 2001-0100507 A * | 6/2003 |
| RU | 2058147 C1 * | 4/1996 |
| WO | 98/29112 A1 | 7/1998 |
| WO | 00/27438 A1 | 5/2000 |
| WO | WO 03/084552 A1 | 10/2003 |
| WO | WO 2005/055723 A1 | 6/2005 |
| WO | WO 2007/081455 A2 | 7/2007 |
| WO | WO 2007/087461 A2 | 8/2007 |

OTHER PUBLICATIONS

CDC Fact Sheet Bacterial Vaginosis Dec. 2007.*
Sobel, Drugs 2003, 63, 1059-1066).*
CDC Fact Sheet Trichomoniasis, Dec. 2007.*
Prutting et al. Infections Diseases in Obstetrics and Gynecology,1998, 6, 191-194.*
Sobel et al. Clinical Infectious Diseases 1997, 24, 649-52).*
Romano et al. Journal of Antimicrobial Chemotherapy 2005, 55, 110-114.*
Andersch B, et al., Bacterial vaginosis and the effect of intermittent prophylactic treatment with an acid lactate gel, Gynecol Obstet Invest, 1990; 30:114-119.
ASTM method (Designation E 2562-07), 2011.
Auler Me, et al. Biofilm formation on intrauterine devices in patients with recurrent vulvovaginal candidiasis, Med Mycol, 2010; 48:211-216.
Centers for Disease Control and Prevention. Sexually Transmitted Diseases Treatment Guidelines, MMWR 2010; 59 (No. RR-12):56-58.
Ejernaes K., Bacterial characteristics of importance for recurrent urinary tract infections caused by *Escherichia coli*, Dan Med Bull, 2011; 58:B4187.
Fong Iw, The value of chronic suppressive therapy with itraconazole versus clotrimazole in women with recurrent vaginal candidiasis, Genitourin Med, 1992; 68:374.
Galli J, et al., Biofilm formation by *Haemophilus influenza* isolated from adeno-tonsil tissue samples, and its role in recurrent adenotonsillitis, Acta Otorhinolaryngol Ital, 2007; 27:134-138.
Goller CC, et al. Revising the *Escherichia coli* polysaccharide capsule as a virulence factor during urinary tract infection, Virulence, 2010; 1:333-337.
Harmanli Oh, et al., Urinary tract infections in women with bacterial vaginosis, Obstet Gynecol, 2000; 95:710.
Kirjavainen PV, et al., Abnormal Immunological Profile and Vaginal Microbiota in Women Prone to Urinary Tract Infections, Clin Vaccine Immunol, 2009; 29-36.
Miller KV, et al., Recurrent enterococcal endophthalmitis seeded by an intraocular lens biofilm, J Cataract Refract Surg, 2011; 37:1355-1359.
Minardi D, et al., Urinary tract infections in women: etiology and treatment options, Int J Gen Med, 2011; 4:333-343.
Patterson JL, et al., Analysis of adherence, biofilm formation and cytotoxicity suggests a greater virulence potential of *Gardnerella vaginalis* relative to other bacterial vaginosis-associated anaerobes, Microbiology, 2010; 156:392-99.

(Continued)

*Primary Examiner* — James H Alstrum Acevedo
*Assistant Examiner* — Jessica Kassa
(74) *Attorney, Agent, or Firm* — Wood, Phillips, Katz, Clark & Mortimer

(57) ABSTRACT

The present invention generally relates to methods and compositions for treating pathogenic vaginal biofilms. More specifically, the invention relates to pharmaceutical compositions comprising a combination of boric acid and diethylaminetetracetic acid (EDTA) and to methods of using such compositions to treat or prevent biofilm formation associated with vaginal infections, such as bacterial vaginosis (BV), vulvovaginal candidiasis (VVC), trichomoniasis or mixed infections.

18 Claims, 4 Drawing Sheets

OTHER PUBLICATIONS

Reichman et al., Boric acid addition to suppressive antimicrobial therapy for recurrent BV, Sexually Transmitted Diseases, 2009; 36: 1-3.

Rosen DA, et al., Detection of intracellular bacterial communities in human urinary tract infection, Plos Med, 2007; 4:1949-1958.

Shahid Z, et al., Reduced fluconazole susceptibility of *Candida albicans* isolates in women with recurrent vulvovaginal candidiasis: effects of long-term fluconazole therapy, Diagn Microbiol Infect Dis, 2009; 64:354-356.

Sharami SH, et al., Urinary tract infections in pregnant women with BV, J Obstet Gynaecol, 2007; 27:252-254.

Sobel JD, et al, Suppressive antibacterial therapy with 0.75% metronidazole vaginal gel to prevent recurrent bacterial vaginosis, Am J Obstet Gynecol, 2006; 194:1283-1289.

Sumati AH, et al., Association of urinary tract infection in women with bacterial vaginosis, J Glob Infect Dis, 2009; 1:151-152.

Swidsinski A, et al., Adherent biofilms in bacterial vaginosis, Obstet Gynecol, 2005; 106:1013-23.

Swidsinski A, et al., An adherent *Gardnerella vaginalis* biofilm persists on the vaginal epithelium after standard therapy with oral metronidazole, Am J Obstet Gynecol, 2008; 198:97.

Swidsinski A, et al., *Gardnerella* biofilm involves females and males and is transmitted sexually, Gynecol Obstet Invest, 2010; 70:256-263.

Swidsinski A, et al., Response of *Gardnerella vaginalis* biofilm to 5 days of moxifloxacin treatment, FEMS Immunol Med Microbiol, 2011; 61:41-46.

Zuliani G, et al., Biofilm density in the pediatric nasopharynx: recurrent acute otitis media versus obstructive sleep apnea, Ann Otol Rhino! Laryngol, 2009; 118:519-524.

Liang Yimin et al., "Eye drop containing rich oxygen and preparation thereof", EPODOC 1998, XP002242055.

Supplemental European Search Report for corresponding European Patent Application No. EP 08 85 3908 dated Dec. 3, 2010.

Alsaif "Inhibition of gastric mucosal damage by boric acid pretreatment in rats", J. Med. Sci. Apr.-Jun. 2004, 4 pp. 102-109.

Barranco et al., "Cellular changes in boric acid-treated DU-145 prostate cancer cells", British Journal of Cancer, 2006, 94 pp. 884-890.

Clindesse® (clindamycin phosphate) vaginal cream, 2% prescribing information, pp. 1-2, Nov. 2004.

Dzondo-Gadet et al., "Action ofboron at the molecular level, effects on transcription and translation in an acellular system", Biol. Trace Elem. Res., 2002, 85 pp. 23-32.

Flagyl® ER (metronidazole extended release tablets) prescribing information, pp. 1-11, 2006.

Kikuchi et al., "Mechanism of permeability-enhancing effect of EDTA and boric acid on the corneal penetration of CS-088", International Journal of Pharmaceutics, 2005, 299 pp. 107-114.

Kim et al., "Boric acid inhibits adenosine diphosphate-ribosyl cyclase non-competitively", Journal of Chromatography A., 2006, 1115 pp. 246-252.

Meers et al., "Bacteriostatic and bactericidal actions of boric acid against bacteria and fungi commonly found in urine", J. Clin. Pathol. 1990, 43 pp. 484-487.

MetroGel-Vaginal® (metronidazole vaginal gel) 0.75% Vaginal Gel, prescribing information, pp. 1-6, Jan. 2003.

Prutting et al., "Boric acid vaginal suppositories: a brief review", Infectious Diseases in Obstetrics and Gynecology, 1988, 6 pp. 191-194.

Pybus et al., "Evidence for a commensal, symbiotic relationship between *Gardnerella vaginalis* and *Prevotella bivia* involving ammonia: potential significance for bacterial vaginosis", Journal of Infectious Disease 1997, 175 pp. 406-413.

Rodu et al., "In vitro virucidal activity by components of a topical film-forming medication" J. Oral Pathol. 1988, 17 pp. 324-326.

Shubair et al., "Growth inhibition of *Candida albicans* and other medically important yeasts by vaginal contraceptive products", Gynecol. Obstet. Invest. 1990, 29 pp. 67-70.

Skinner et al., "Possible treatment for cold sores", British Medical Journal Sep. 22, 1979, pp. 704.

Sobel et al., "Suppressive antibacterial therapy with 0.75% metronidazole vaginal gel to prevent recurrent bacterial vaginosis", American Journal of Obstetrics and Gynecology 2006, 194 pp. 1283-1289.

Swidsinski et al., "An adherent *Gardnerella vaginalis* biofilm persists on the vaginal epithelium after standard therapy with oral metronidazole" American Journal of Obstetrics and Gynecology 2007, pp. 1.e1-1.e6.

Thiex et al., Determination of crude protein in animal feed, forage, grain and oilseeds by using block digestion with a copper catalyst and steam distillation into boric acid: collaborative study, Journal of AOAC International, 2002, vol. 85 No. 2 pp. 309-317.

Verstraelen, "Cutting edge: the vaginal microflora and bacterial vaginosis", Verh. K. Acad. Geneeskd. Belg. 2008, 70(3) pp. 147-174.

\* cited by examiner

COMPOSITIONS AND METHODS FOR TREATING VAGINAL INFECTIONS AND PATHOGENIC VAGINAL BIOFILMS

FIELD OF THE INVENTION

The invention generally relates to compositions and methods for treating vaginal infections and pathogenic vaginal biofilms.

BACKGROUND OF THE INVENTION

According to the Centers for Disease Control (CDC), vaginitis is an extremely common diagnosis among women of reproductive age, resulting in more than 10 million medical office visits every year. The vast majority of cases of vaginitis are related to one of three infections: bacterial vaginosis (BV), vulvovaginal candidiasis (VVC) (aka "vaginal yeast infection"), and trichomoniasis. Bacterial vaginosis accounts for approximately 40-45% of all infections, while VVC and trichomoniasis account for about 20-25% and 15-20%, respectively. In some instances, the etiology of vaginitis may be mixed. Unfortunately, national surveillance data on vaginitis are lacking, as none are reportable diseases; however, prevalence estimates by the National Health and Nutrition Examination Survey for BV show that nearly one-third (29%) of women in the general U.S. population between the ages of 14-49 years of age are positive for this infection.

Although a number of FDA-approved therapies are available for the management of vaginitis, treatment is often challenging and further complicated by the increasing rates of treatment-resistant organisms and recurrent and persistent infections. In addition, there is a growing body of scientific evidence that identifies these infections as important risk factors for more serious health complications, particularly during pregnancy. Estimates of the direct cost of vaginitis for medical office visits and self treatment are reportedly more than $1 billion annually; however, indirect costs related to secondary complications (e.g., morbidity in pregnancy, pelvic inflammatory disease, and postoperative infections) and lost work productivity are far greater.

Accordingly, the public health implications of these infections are significant, and there is a need for improved therapeutic approaches.

Biofilm-related infections were first described in 1978 and are now believed to be a causative factor in more than 60% of human infections, particularly in their persistence and recurrence. Biofilms have been described for a wide range of chronic infections caused by bacterial and fungal organisms, including skin wounds and burns, otitis media, periodontal disease, endocarditis, urinary tract infections and device-related infections (e.g., catheters, heart valves), but are not recognized as important in the causation of vaginal infections and, thus, have not been addressed in practice by those skilled in the art of treating vaginitis.

Biofilms are highly organized populations of microorganisms embedded in a protective exopolysaccharide (i.e., carbohydrate) matrix that adhere to inert and living membrane surfaces (i.e., sessile populations) by way of adhesion proteins. In contrast to their free-floating or "planktonic" counterparts, biofilm-associated microorganisms are notoriously resistant to antimicrobial therapy—up to 1000-fold or greater—and are a source of many recurrent and recalcitrant infections. It is believed that their persistence is related, in part, to the up regulation of genes that confer a highly distinct and resistant biofilm phenotype that perpetuates growth and survival of the biofilm community. This includes the formation of biofilm matrix material, which restricts antimicrobial penetration and interferes with normal host defense mechanisms, and the generation of "persister" organisms that are essentially intolerant to killing.

The ability of biofilms to migrate over solid surfaces away from areas of high stress—a capability known as swarming—and their slow rate of growth are also believed to contribute to their pathogenicity and persistence. Evidence further suggests that established biofilms play a role in the persistence of other secondary pathogens, such as viruses, by acting as protective reservoirs that shield these organisms from destruction by the immune system and conventional antimicrobial therapies.

Boric acid or boracic acid [$B(OH)_3$] is a weak inorganic acid with weak antimicrobial properties. In vitro, boric acid is weakly fungistatic against clinical isolates of *C. albicans* as well as non-albicans species, including *C. tropicalis, C. glabrata* and *C. parapsilosis* (Shubair, 1990; Prutting 1998). While boric acid also displays bacteriostatic activity in vitro against a range of common bacterial pathogens, including staphylococci and streptococci, *P. aeruginosa, E. coli*, and *Proteus, Klebsiella* and *Enterobacter* species (Meers 1990), the antibacterial effects of boric acid are slow acting and, in contrast to many antibiotics, appear to be independent of cell growth as dividing and stationary-phase cells have been shown to be equally affected (Meers 1990). The weak antimicrobial properties of boric acid render it surprising that boric acid would be effective in the treatment of vaginal infections, particularly those that are resistant, persistent and recurrent in nature.

Boric acid also displays other biological effects. For example, boric acid has been shown to play a role in the modulation of calcium and to stimulate wound healing through action on extracellular matrix formation and synthesis of growth factors (Dzondo 2002). Boric acid has also been shown to have anti-proliferative effects in prostate cancer cell lines and cytoprotective effects in animal models of gastric injury (Barranco 2006); (Alsaif 2004). There is also evidence to further suggest that boric acid has antiviral activity, specifically against herpes simplex virus (Skinner 1979; Rodu 1988). On a molecular level, boric acid binds cis-diol compounds, including membrane polysaccharides and carbohydrate moieties of nucleic acids involved in cell metabolism and signaling (e.g., RNA, NAD, ATP), which may explain in part the reported effects of boric acid on membrane and cellular functioning (Kim 2006); whereas the combination of boric acid and ethylene-diamine-tetra-acetic acid (EDTA) has demonstrated a unique synergy on corneal membrane permeability in vitro (Kikuchi 2005).

SUMMARY OF THE INVENTION

The invention generally relates to the surprising discovery that boric acid may be used to treat and/or prevent vaginal infections due to its role as a vaginal biofilm disrupter. We postulate that biofilms play an important role in vaginal infections, specifically in vaginitis, and more specifically, in bacterial vaginosis (BV), vulvovaginal candidiasis (VVC) (aka "vaginal yeast infection"), and trichomoniasis.

In one embodiment, the invention relates to a pharmaceutical composition for treating and/or preventing vaginal infections and/or pathogenic vaginal biofilms comprising boric acid and ethylene-diamine-tetra-acetic acid (EDTA).

The amount of boric acid in the pharmaceutical compositions of the invention is preferably from about 0.01 mg to about 10 g, more preferably from about 0.1 mg to about 1 g, and even more preferably from about 1 mg to about 250 mg.

The amount of EDTA in the pharmaceutical compositions of the invention is preferably from about 0.001 mg to about 1 g, and more preferably from about 0.01 mg to about 250 mg.

In one embodiment, the relative amount of boric acid to EDTA is in the range of from about 1:1 to about 1000:1 on a weight basis.

In another embodiment, the relative amounts of EDTA and boric acid are in the range of from about 2:1 to 100:1.

In another embodiment, the pharmaceutical compositions of this invention further comprise one or more bioactive agents selected from the group consisting of bergamot oil, tea tree oil or other essential oils, zinc ion, and gallium.

In another embodiment, the pharmaceutical compositions of this invention further comprise at least one additive selected from the group consisting of gelling agents, buffers, preservatives, surfactants, detergents, oils, alcohols, emulsifiers, solubilizers, humectants, and bioadhesives.

In one embodiment, the pharmaceutical compositions of this invention further comprise a pharmaceutically acceptable carrier suitable for vaginal and/or vulvar drug administration.

In another embodiment, the invention relates to a method of treating and/or preventing vaginal infections and/or pathogenic vaginal biofilms comprising administering to a patient in need thereof a therapeutically effective amount of boric acid in the absence of any therapeutic amount of acetic acid.

In another embodiment, the invention relates to a method of treating and/or preventing a vaginal infection and/or pathogenic vaginal biofilms comprising administering to a patient in need thereof a therapeutically effective amount of a pharmaceutical composition comprising boric acid and EDTA.

In one embodiment, the methods of this invention comprise applying the pharmaceutical compositions to a vagina and/or a vulva from once a day to three times a day.

In another embodiment, the methods of this invention comprise applying the pharmaceutical compositions to a vagina and/or a vulva intermittently, such as twice weekly, as prophylaxis.

In another embodiment, the pharmaceutical compositions of the invention are applied topically to a vagina and/or a vulva of a patient.

The pharmaceutical compositions may be applied in the form of a suppository, an ointment, cream, solid (e.g., tablet, capsule, ovule, suppository), solution, suspension, gel, foam, film or liposomal composition. The pharmaceutical compositions may also be contained within a vaginal ring, tampon, suppository, sponge, pillow, puff, or osmotic pump system.

The pharmaceutical compositions of the invention can be co-administered with other pharmaceutically active compounds, as for example, with metronidazole.

The dosage forms of the pharmaceutical compositions may also be formulated in a sustained-release form, employing various polymers, fibers, resins, waxes, oils, or other pharmaceutical excipients used by those skilled in the art of medicinal chemistry to produce a prolonged release of the active constituents of the pharmaceutical compositions.

In one embodiment, the vaginal infection is a bacterial infection.

In another embodiment, the vaginal infection is vulvovaginal candidiasis.

In yet another embodiment, the vaginal infection is trichomoniasis.

In yet another embodiment, the vaginal infection is a viral infection.

If not properly treated, vaginal infections may result in urinary tract infections. Thus, in another embodiment, the invention relates to the treatment and prevention of urinary tract infections.

In yet another embodiment, the vaginal infection is caused by two or more pathogens selected from the group consisting of bacteria, fungi, parasites, and viruses and is referred to as a mixed infection.

In another embodiment, the invention relates to an article of manufacture comprising packaging material and a pharmaceutical composition of the invention within the packaging material. The pharmaceutical composition is present in an amount sufficient to treat a vaginal infection or pathogenic vaginal biofilms in a patient, preferably in an amount equivalent to at least one unit dose. The packaging material comprises a label that indicates that the pharmaceutical composition can be used for treating vaginal infections and associated pathogenic vaginal biofilms. Preferably the label includes other printed indicia such as a listing of ingredients, the manufacturer's name and address, and the like. Preferably the packaging material also includes a printed insert including detailed information on the composition, its method of administration for treatment of vaginal infections and pathogenic biofilms, side effects, contraindications, and the like indicia, which may be required by governmental agencies responsible for regulation of pharmaceutical products.

DETAILED DESCRIPTION OF THE INVENTION

Definitions

Figure 1:
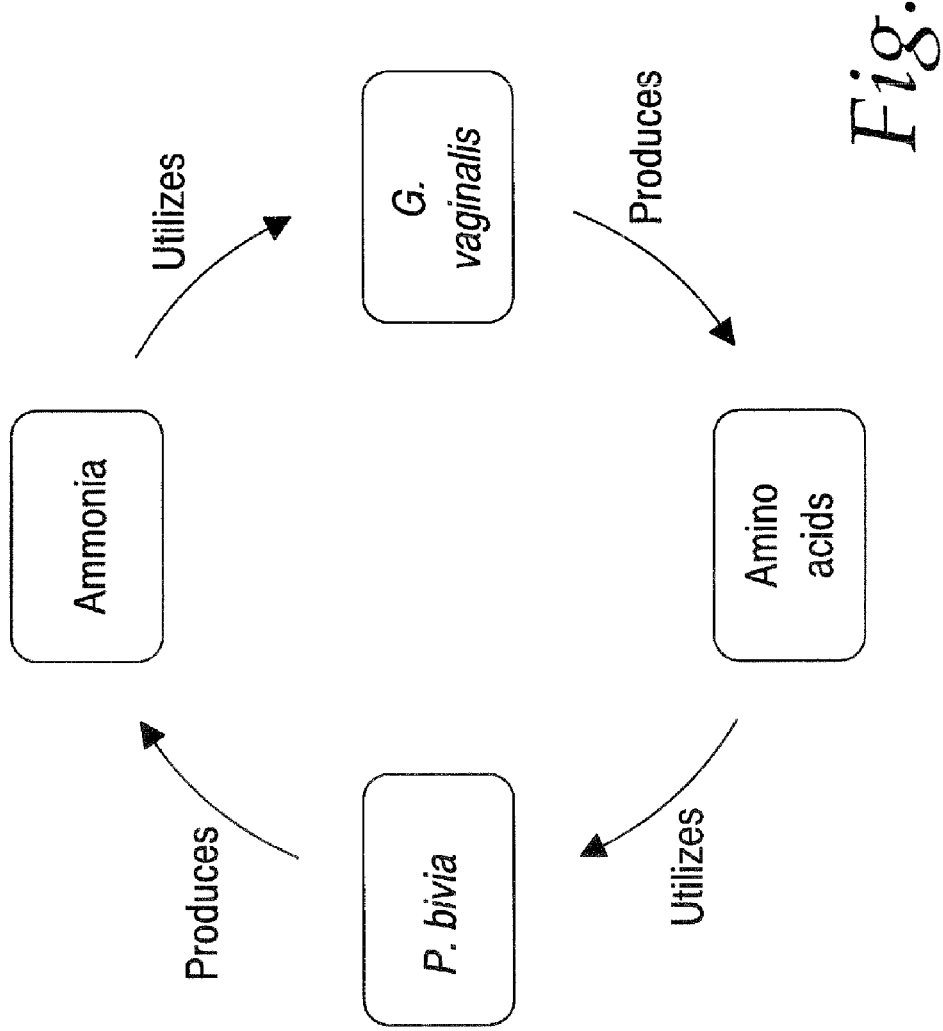
FIG. 1 is a diagram that illustrates a symbiotic relationship of BV pathogens.

A "biofilm" as used herein refers to a surface-attached, highly structured, single- or multi-species population of microorganisms enmeshed in a self-produced exopolysaccharide matrix that facilitates adherence, colonization and growth on a surface, such as the vaginal mucosa, and displays a distinct biofilm phenotype.

When referring to a compound as an active agent, applicants intend the term "compound" or "active agent" to encompass not only the specified molecular entity but also its pharmaceutically acceptable, pharmacologically active salts.

The terms "treating" and "treatment" as used herein refer to causing a reduction in severity and/or frequency of symptoms, elimination of symptoms and/or underlying cause, prevention of the occurrence of symptoms and/or their underlying cause, and/or improvement. Thus, "treating" a patient with said compositions of the invention includes prevention of a particular disorder in a susceptible individual, as well as management of a clinically symptomatic individual to inhibit or cause regression of a disorder or disease. Treatment can include prophylaxis, therapy, or cure. For example, treatment of a biofilm encompasses prevention of formation of a biofilm in a patient susceptible to development of a biofilm as well as treatment of a patient with a biofilm by inhibiting, controlling or causing regression of the underlying disease.

The term "vagina" as used herein is intended to be inclusive of the vaginal region generally, including also the vulva, vestibule, and the cervix.

The term "vaginal infection" includes any infectious disorder, including biofilm-associated infections, of any vaginal area, including the vulva, vestibule, and the cervix. The term also encompasses plural vaginal infections.

The term "disrupting" is intended to encompass inflicting any and all damage to biofilms.

The term "therapeutically effective amount" of the pharmaceutical compositions of the invention refers to a sufficient amount of the composition to treat disorders, at a reasonable benefit/risk ratio applicable to any medical treatment. It will be understood, however, that the total daily usage of the compositions of the present invention will be decided by the attending physician within the scope of sound medical judgment. The specific effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the composition at levels lower than required to achieve the desired therapeutic effect and to gradually increase the dosage until the desired effect is achieved.

As used in this specification and the appended claims, the singular forms "a," "an" and "the" include plural referents unless the context clearly dictates otherwise. Thus, for example, reference to "a bioactive agent" includes a mixture of two or more bioactive agents, reference to "a pharmaceutically acceptable excipient" includes mixtures of such excipients, and the like.

The invention relates to a pharmaceutical composition for treating and/or preventing a vaginal infection and/or pathogenic vaginal biofilms comprising boric acid and EDTA.

The amount of boric acid in the pharmaceutical compositions of the invention is preferably from about 0.01 mg to about 10 g, more preferably from about 0.1 mg to about 1 g, and even more preferably from about 1 mg to about 250 mg.

The amount of EDTA in the pharmaceutical compositions of the invention is preferably from about 0.001 mg to about 1 g, and more preferably from about 0.01 mg to about 250 mg.

In one embodiment, the relative amount of boric acid to EDTA is in the range of from about 1:1 to about 1000:1 on a weight basis.

In another embodiment, the relative amounts of EDTA to boric acid are in the range of from about 2:1 to 100:1.

The pharmaceutical compositions of this invention may further comprise one or more bioactive agents selected from the group consisting of bergamot oil, tea tree oil or other essential oils, zinc ion, and gallium. These bioactive agents may enhance and/or complement the biofilm-disrupting effects of boric acid and EDTA.

For example, gallium may be added to the pharmaceutical composition to enhance the biofilm disruption effects of boric acid and EDTA by targeting the iron metabolism of pathogenic microorganisms and interfering with its signaling role in the formation of biofilms.

Zinc ion or a salt thereof may be added to enhance the biofilm disrupting effect of boric acid and EDTA.

Surfactants may be added to the pharmaceutical compositions. The surfactants may provide for better surface contact of the compositions with the vaginal mucosa by further reducing surface tension and promoting dispersal of the active substances, or may possess anti-biofilm properties that may complement those of said boric acid and EDTA compositions. Surfactants that may be added include but are not limited to lauryl sulfate and teepol, and the like.

The pharmaceutical compositions of this invention may further comprise other additives such as gelling agents, buffers, preservatives, detergents, oils, alcohols, emulsifiers, solubilizers, humectants, and bioadhesives.

The pharmaceutical compositions of this invention further comprise a pharmaceutically acceptable carrier suitable for vaginal and/or vulvar drug administration.

The compositions of the present invention may include a physiologically tolerable preservative.

Suitable physiologically tolerable preservatives include bacteriostats, preservatives, inhibitors, and the like, such as methyl, ethyl, propyl, and butyl esters of parahydroxybenzoic acid (paraben); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide, the cis isomer of 1-(3-chloroallyl-3,5,7-triaza-1-azanidadamantane chloride; hexachlorophene; sodium benzoate; phenolic compounds such as butyl hydroxyanisol, butyl hydroxytoluene, chloro- and bromo-cresols, and chloro- and bromo-oxylenols; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like. Preferably, the preservative is included in an amount in the range of about 0.05 to about 0.2 weight percent, on a total composition weight basis.

Pharmaceutically acceptable excipients that can be included in the pharmaceutical compositions of the present invention include, for example, physiologically tolerable surfactants, solvents, emollients, colorants, fragrances, and the like, which are well known in the art. The compositions preferably have a pH value in the range of about 3.5 to about 7, more preferably in the range of about 4 to 4.5.

The invention also relates to a method of treating and/or preventing vaginal infections and/or pathogenic vaginal biofilms comprising administering to a patient in need thereof a therapeutically effective amount of boric acid.

The invention also relates to a method of treating and/or preventing vaginal infections and/or pathogenic vaginal biofilms comprising administering to a patient in need thereof a therapeutically effective amount of boric acid and EDTA.

Without being bound to any specific theory, it is believed that boric acid may act by binding preferentially with cis-diol carbohydrate components of the pathogenic biofilm matrix and stimulating the synthesis of protease enzymes, thereby disrupting the structural integrity of the biofilm and its adherence to the vaginal mucosa. Boric acid may also offer an additional advantage in BV biofilms because of its ability to chemically "trap" ammonia by forming ammonium borate (Thiex N J et al. 2002). The relevance of this relates to the symbiotic relationship described for *G. vaginalis*, the primary bacterial constituent of BV biofilms, and *P. bivia*—a secondary BV pathogen (Pybus 1997). In vitro research suggests that *G. vaginalis* thrives off the ammonia by-products of *P. bivia* metabolism while *P. bivia* thrives off the amino acid by-products of *G. vaginalis* metabolism. FIG. 1 shows this symbiotic relationship in the form of a diagram. Accordingly, vaginal administration of boric acid may interrupt this symbiosis by trapping ammonia and depleting the vaginal microenvironment of essential BV nutrients required for bacterial growth and biofilm formation and survival.

The invention also relates to a method of treating and/or preventing a vaginal infection comprising administering to a patient a therapeutically effective amount of a pharmaceutical composition comprising boric acid and EDTA.

The amount of boric acid in the pharmaceutical compositions of the invention is preferably from about 0.01 mg to about 10 g, more preferably from about 0.1 mg to about 1 g, and even more preferably from about 1 mg to about 250 mg.

The amount of EDTA in the pharmaceutical compositions of the invention is preferably from about 0.001 mg to about 1 g, and more preferably from about 0.01 mg to about 250 mg.

In one embodiment, the relative amount of boric acid to EDTA is in the range of from about 1:1 to about 1000:1 on a weight basis.

In another embodiment, the relative amount of EDTA to boric acid is in the range of from about 2:1 to 100:1.

In one embodiment, the methods of this invention comprise applying the pharmaceutical compositions to a vagina and/or a vulva from once a day to three times a day.

In another embodiment, the methods of this invention comprise applying the pharmaceutical compositions to a vagina and/or a vulva intermittently, such as twice weekly, as prophylaxis.

The pharmaceutical compositions of the invention are applied topically to a vagina and/or a vulva of a patient.

The pharmaceutical compositions may be applied in the form of a suppository, an ointment, cream, solid (e.g., tablet, capsule, ovule, and suppository), solution, suspension, gel, foam, film, or liposomal composition. Ointments and creams, may, for example, be formulated with an aqueous or oily base with the addition of suitable thickening and/or gelling agents. One technique for applying the compositions of the claimed invention is to employ a single use packet (such as a small envelope-like structure, or the like) containing an intended single unit dose. The packet is initially sealed, but is opened at the time of use by tearing, cutting, or the like at a desired or planned location in the packet after which the contents are directly administrable as labeled.

The pharmaceutical compositions may also be contained within a vaginal ring, tampon, suppository, sponge, pillow, puff, or osmotic pump system.

The pharmaceutical compositions of the invention can be co-administered with other pharmaceutical compositions, for example, with metronidazole.

The dosage forms of the pharmaceutical compositions may also be formulated in a sustained-release form, employing various polymers, fibers, resins, waxes, oils, or other pharmaceutical excipients used by those skilled in the art of medicinal chemistry to produce a prolonged release of the active constituents of the pharmaceutical compositions.

In one embodiment, the vaginal infection is a bacterial infection.

In another embodiment, the vaginal infection is vulvovaginal candidiasis.

In yet another embodiment, the vaginal infection is trichomoniasis.

In yet another embodiment, the vaginal infection is a viral infection.

If not properly treated, vaginal infections may result in urinary tract infections. Thus, in another embodiment, the invention relates to the treatment and prevention of urinary tract infections.

In yet another embodiment, the vaginal infection is caused by two or more pathogens selected from the group consisting of bacteria, fungi, parasites, and viruses.

The methods and pharmaceutical compositions can be used in combination with other antimicrobial therapies, including antibacterial, antifungal, antiparasitic or antiviral agents, to potentiate their antimicrobial efficacy and/or reduce their dosage requirements when employed for the treatment of vaginal infections associated with biofilm formation.

In addition, the methods and the pharmaceutical compositions of the invention may also be used as a carrier material for other medicines, such as antibiotics, antifungals, antiparasitics and anti-inflammatories, thereby further broadening the compositions' medical efficacy.

The total daily dose of the compositions of this invention administered to a human or lower animal may range from about 100 mg to about 15 g/day. More preferable doses can be in the range of from about 500 mg to about 5 g/day. If desired, the effective daily dose can be divided into multiple doses for purposes of administration; consequently, single dose compositions may contain such amounts or submultiples thereof to make up the daily dose.

The invention also relates to an article of manufacture comprising packaging material and a pharmaceutical composition of the invention within the packaging material. The pharmaceutical composition is present in an amount sufficient to treat a vaginal infection and/or disrupt a pathogenic vaginal biofilm in a patient, preferably in an amount equivalent to at least one unit dose. The packaging material comprises a label that indicates that the pharmaceutical composition can be used for treating vaginal infections and/or disrupting a pathogenic vaginal biofilm. Preferably, the label includes other printed indicia such as a listing of ingredients, the manufacturer's name and address, and the like. Preferably, the packaging material also includes a printed insert including detailed information on the composition, its method of administration for treatment of pathogenic vaginal biofilms and vaginal infections, side effects, contraindications, and the like indicia, which may be required by governmental agencies responsible for regulation of pharmaceutical products.

As the Examples show, provided compositions and methods demonstrate unexpectedly advantageous properties of the methods and pharmaceutical compositions according to the invention. The Examples are presented for illustrative purposes only and are not meant to limit the invention unless otherwise stated in the claims.

EXAMPLE 1

Disruption of *C. albicans* and *G. vaginalis* biofilms by Boric Acid and EDTA

A) Experimental Methods:

The biofilm disrupting effects of boric acid and EDTA at various test concentrations, alone and in combination, against *C. albicans* and *G. vaginalis* biofilms were studied in vitro using CDC biofilm reactors (Biosurface Technologies Corporation). The experiments were carried out at the Center for Biofilm Engineering in Bozeman, Mont. The CDC biofilm reactor method was selected based on its reproducibility and ability to provide consistent biofilm samples and growth conditions necessary for the evaluation of antimicrobial agents. As a prelude to the biofilm experiments, the planktonic (i.e., free-floating vs. biofilm-associated) MIC values for boric acid and EDTA against both test organisms were established utilizing standard MIC methodologies. In contrast to *C. albicans*, the planktonic MIC values for boric acid and EDTA against *G. vaginalis* had not previously been reported.

The CDC reactor consists of eight polycarbonate coupon holders suspended from a ported lid. Each holder accommodates 3 separate coupons. The lid with coupon holders and coupons, 24 in total, is mounted in a 1 liter glass vessel with a side-arm discharge port. Biofilms are formed by circulating liquid growth media through the vessel while mixing and shear force is generated by a magnetic stir bar/vane rotated by a magnetic stir plate.

In preparation of the biofilm experiments relating to the invention, overnight cultures of *C. albicans* and *G. vaginalis* were prepared by adding 1 mL frozen stock to 9 mL growth media (either *G. vaginalis* ATCC #14018 in 50% BHI broth+1% starch, or *C. albicans* ATCC #96113 in 50% SD broth+1% sucrose) and incubated for 24 hours at 37° C., *C. albicans* was grown under atmospheric conditions while *G. vaginalis* was grown with the addition of 5% $CO_2$.

Once the overnight cultures were ready, 24 polycarbonate coupons were placed in the CDC biofilm reactor coupon holders and secured using a screwdriver. The influent/effluent tubing ends were then foiled and clamped, and the entire vessel autoclaved for 20 minutes. The appropriate medium was added directly into the reactor up to the effluent sidearm (approximately 350 mL). The reactor was then inoculated with 4 mL of overnight culture. To facilitate optimal biofilm growth, *C. albicans* reactors were incubated under atmospheric conditions at 37° C., with continuous stirring at the lowest setting for 24 hours. *G. vaginalis* reactors were placed in a 5% $CO_2$ incubator with continuous stirring at the lowest setting for 120 hours. This phase of biofilm formation is referred to as "batch mode." After the batch mode was completed, growth medium flow was initiated at 1 mL/min for an additional 24 hours via a peristaltic pump.

Next, the 24 biofilm-covered coupons were aseptically removed from the CDC reactor and placed in a 24-well plate, with each well containing 2 mL of test solution. The test solutions were run in triplicate and included varied concentrations of boric acid (BA) and EDTA or a combination thereof. A growth control and an active control—based on current treatment standards for the respective infections—were also included. Fluconazole at a concentration of 8 μg/mL was selected as the treatment control for *C. albicans*. This represents the higher end of the range of drug levels achieved in biologic fluids and tissues (4.12-8.08 μg/mL), including vaginal secretions and tissues, following oral dosing of fluconazole at a maximum daily dose of 400 mg (more than double the current FDA-approved dose for vaginal candidiasis). The active control for *G. vaginalis* was metronidazole at a concentration of 192 μg/mL. This concentration was based in part on the planktonic MIC value of metronidazole against *G. vaginalis* that was found in this study (128 μg/mL), and represents a conservative level that falls on the higher end of MIC values reported by other investigators. Note also that this level is more than 8 times higher than peak systemic levels of metronidazole achieved with the approved 750-mg BV regimen (Flagyl ER®).

Each test solution was dissolved in the appropriate medium and filter sterilized before use. The plates were then incubated for 24 hours under appropriate growth conditions. After the 24-hour treatment period, all coupons were rinsed by removing the solution in the well and adding 2 mL of sterile phosphate buffered saline (PBS). The procedure was repeated for a total of two rinses. The coupons were then aseptically transferred to a sterile 15 mL conical vial containing 10 mL of sterile PBS. The tubes were vortexed for 30 seconds, sonicated for 2 minutes and then vortexed for an additional 30 seconds. The cells suspension was serially diluted and plated on agar (SD agar for *C. albicans* and BHI+1% starch for *G. vaginalis*). The plates were incubated for 24-48 hours and the colonies counted. Results were reported as number of colony forming units (cfu) per $cm^2$ and mean log reductions in biofilm load relative to untreated biofilm controls.

B) Biofilm Disruption:

In these experiments, boric acid and EDTA displayed profound effects on established biofilms, well beyond that observed for active controls and consistently above the 3-log threshold required for effective killing (i.e., bactericidal vs. bacteriostatic activity). In fact, neither of the active controls—both FDA-approved antimicrobials—had an appreciable impact on the respective pathogenic biofilms.

Figure 2:
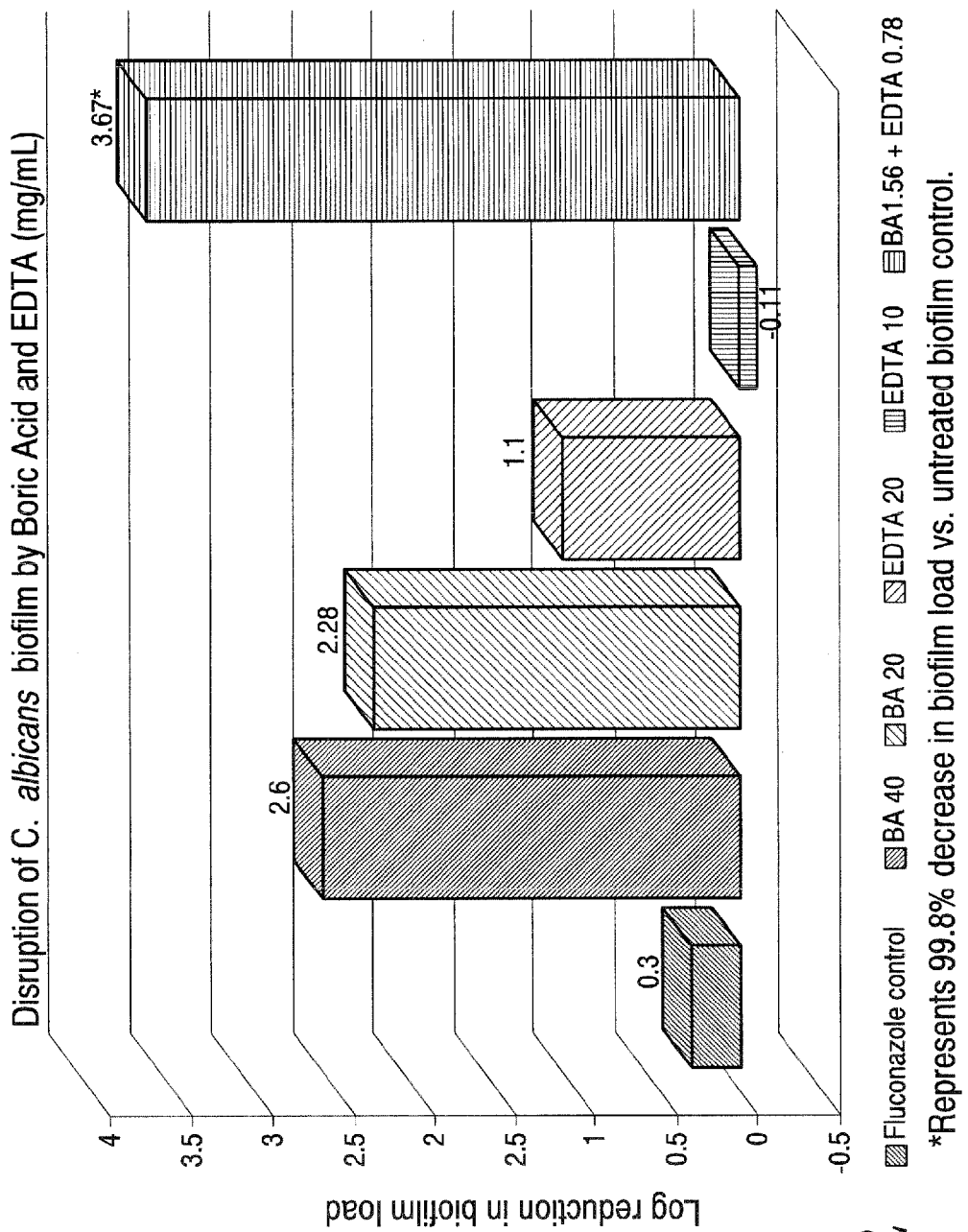
FIG. 2 is a chart that illustrates the effect of boric acid and EDTA on *C. albicans* biofilm in terms of log reduction in biofilm load vs. untreated biofilm controls.

For *C. albicans*, a synergistic effect was observed for the combination of boric acid and EDTA as shown in FIG. 2.

FIG. 2 is a chart that illustrates the effect of boric acid and EDTA on *C. albicans* biofilm. As FIG. 2 demonstrates, the greatest log reduction in biofilm load of 3.67 $cfu/cm^2$ was achieved when boric acid and EDTA were combined at their planktonic MIC values (1.56 mg/mL and 0.78 mg/mL, respectively) compared with higher concentrations of the individual agents alone. This represents a 99.8% reduction in biofilm load compared with untreated biofilm controls and shows that boric acid, particularly when combined with EDTA, confers fungicidal activity against *C. albicans* biofilms. These findings are remarkable and completely unexpected based on boric acid's weak fungistatic activity against planktonic cells and surprisingly in line with the magnitude of log kill reported for FDA-approved antimicrobials against susceptible planktonic pathogens—generally in the range of about 2-4 log reductions.

Figure 3:
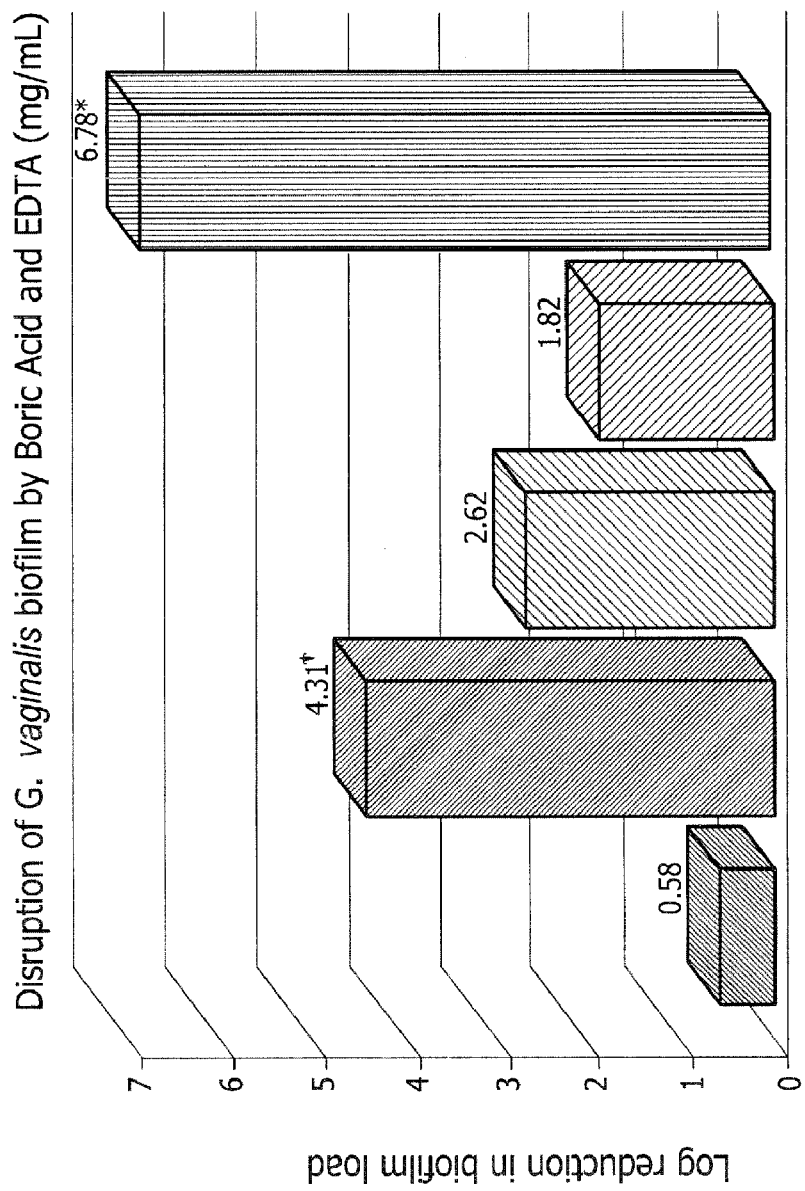
FIG. 3 is a chart that illustrates the effect of boric acid and EDTA on *G. vaginalis* biofilm in terms of log reduction in biofilm load vs. untreated biofilm controls.

Even more impressive results were demonstrated against *G. vaginalis* biofilm, with a clear synergistic effect achieved with combinations of boric acid and EDTA. FIG. 3 is a data chart that illustrates this effect as log reduction in biofilm load. Boric acid at a concentration of 40 mg/mL combined with EDTA at a concentration of 10 mg/mL resulted in complete eradication of the *G. vaginalis* biofilm, whereas the combination of these agents at their low planktonic MIC values—3.125 mg/mL and 0.19 mg/mL respectively—led to a 99.7% decrease in biofilm load vs. untreated biofilm controls. In stark contrast, the metronidazole active control had little impact on the *G. vaginalis* biofilm, and the difference compared with the boric acid and EDTA combinations was quite dramatic. Again, these findings are unprecedented and unpredictable based on the weak antimicrobial properties of boric acid and the planktonic MIC values of these agents against *G. vaginalis* that were established for this study.

The unexpected synergy achieved with the planktonic MIC values of the inventive agents against both *Candida* and *Gardnerella* biofilms is remarkable when considering that bactericidal agents (such as beta lactam antibiotics) require concentrations up to 1000-times higher (or more) than their planktonic MICs to effectively inhibit susceptible organisms in a biofilm mode of growth. These findings support the proposed mechanism of action of boric acid as a biofilm disrupter.

The results are quite remarkable in light of the fact that biofilm disruption would not have been predicted based on the relatively weak antimicrobial activity of these agents and the planktonic MIC values that were established for the first time in this study against *G. vaginalis*.

The therapeutic relevance of these data are three-fold: 1) superior clinical efficacy against biofilm-associated vaginal infections compared with available therapies; 2) improved patient safety with extremely low concentrations of actives and dramatically reduced local and systemic exposure risks; and 3) low potential for the development of secondary infections (particularly vulvovaginal candidiasis), that often complicate vaginitis treatment.

Comparative Example

For comparative purposes, reference is made to a study by Swidsinski, et al, *An adherent Gardnerella vaginalis biofilm persists on the vaginal epithelium after standard therapy with oral metronidazole.* Am J Obstet Gynecol 2008; 198(1): 97.e1-6, which evaluated BV biofilm characteristics on vaginal biopsies following standard oral metronidazole therapy. In this study, 18 patients with BV were treated for 7 days with oral metronidazole, given as 500 mg twice daily and evaluated using standard clinical and microbiologic methods to confirm diagnosis and assess clinical response. Each patient was required to return for a single follow-up visit where they underwent vaginal biopsy, which allowed for the direct visualization of vaginal biofilms using fluorescent in situ hybridization techniques. The women were randomly assigned to return for a follow up visit at one of 6 possible time points at either Day 3 of treatment or at 7, 14, 21, 28 or 35 days after completion of therapy.

Results demonstrated resolution of BV based on standard clinical and microbiologic methods at each time point. Vaginal biopsy results, however, revealed a different picture, showing a persistent accumulation of core pathogenic bacteria, particularly *G. vaginalis* and *Atopobium*, in an adherent biofilm that became more pronounced over time. Notably, all of the *G. vaginalis* isolates that were obtained from these women showed good susceptibility to metronidazole with conventional planktonic MIC testing. This may well explain the low cure rates reported for standard BV therapies and further links these outcomes to the inability of these interventions to effectively disrupt the underlying pathogenic biofilm. The results obtained in this Comparative Example stand in stark contrast to the results demonstrated in the Example, which showed complete eradication of *G. vaginalis* biofilms with a combination of boric acid and EDTA and validated the minimal impact of metronidazole.

EXAMPLE 2

Treatment of Patients with highly refractory, recurrent BV by the use of Boric Acid A retrospective case review was conducted of the use of boric acid in a series of patients with recurrent BV. Boric acid was employed as an antimicrobial agent as part of a 6-month sequential treatment protocol. To qualify for protocol treatment, all of the women had previously failed an induction and long-term maintenance regimen of metronidazole vaginal gel and thus had highly resistant infections.

With the exception of boric acid, all of the other antimicrobials used were FDA approved for BV. The 6-month protocol was as follows:
1. Induction: oral metronidazole or tinidazole twice daily for 7-10 days
2. Boric acid treatment: 600-mg gelatin capsule inserted vaginally daily for 21 days
3. Maintenance: metronidazole vaginal gel twice weekly for 5 months Results at the end of 6 months showed that 77% (24/31) of patients were clinically cured—i.e., asymptomatic and negative for Amsel's clinical criteria for BV. Sixty-seven percent remained cured at 9 months (i.e., 3 months after maintenance). The median duration of remission was 8.7 months. Notably, none of the treatment failures occurred during boric acid therapy and none of the patients experienced a secondary yeast infection or discontinued because of an adverse event or intolerance to any component of the regimen.

To further validate these findings, a prospectively designed clinical study of the use of boric acid in women with highly refractory BV was undertaken. Similar to the retrospective case series, boric acid was employed as an antimicrobial agent as part of a sequential treatment protocol; however, the women enrolled in this study differed from those in the case series in that their infections were even more resistant to treatment-all of the women had failed at least three previous suppressive regimens within 12 months prior to enrollment. Likewise, all patients had florid symptoms of infection, with malodorous discharge and presented with all four clinical diagnostic criteria (Amsel's), including ≧20% clue cells on vaginal wet mount examination.

A total of 58 patients were treated "open label" with standard oral doses of nitroimidazole therapy (metronidazole or tinidazole) twice daily for 7 days followed by boric acid as a 600-mg gelatin capsule inserted vaginally daily for 21 days. Patients determined to be clinically cured were then placed on a maintenance regimen of metronidazole vaginal gel twice weekly for up to 5 additional months.

Figure 4:
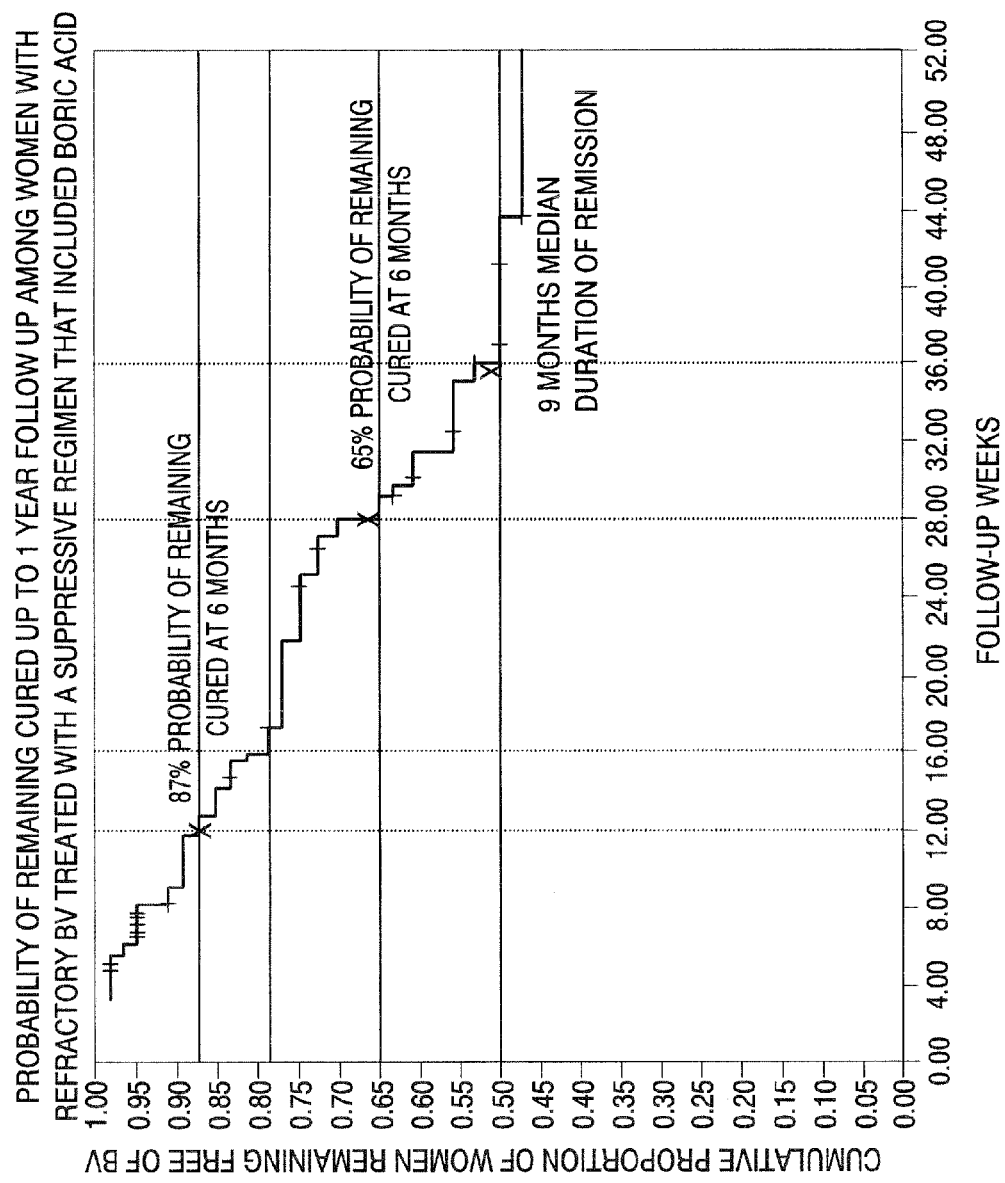
FIG. 4 is a Kaplan-Meier chart that illustrates the cure probability of women with refractory BV that were treated with boric acid.

Impressive results were demonstrated early on with a low rate of clinical failure of 8% following nitroimidazole/boric acid induction. Similarly, breakthrough infections while on metronidazole gel maintenance were exceptionally low, at just 12%. As shown in FIG. 4, the cumulative proportion of cure was surprisingly high in these refractory cases after 12, 16 and 28 weeks—87%, 78% and 65%, respectively. Likewise, the median duration of remission was 9 months, which was similar to that noted in the initial case series (8.7 months).

These findings are most impressive when juxtaposed against the short-term cure rates of 30% to 70% reported for women with primary, uncomplicated BV treated with standard therapies, and the high likelihood of recurrence—up to 80% within 9 months.

Comparative Example

For comparative purposes, reference is made to Sobel J D et al, *Suppressive therapy with 0.750% metronidazole vaginal gel to prevent recurrent bacterial vaginosis,* Am J Obstet Gynecol 2006; 194: 1283-1290 which reported results of a more rigorous controlled clinical study of metronidazole vaginal gel in women with recurrent BV, using a similar treatment protocol to that described for the above Example but without boric acid.

The study involved a 10-day metronidazole vaginal gel induction phase followed by a 4-month twice-weekly maintenance regimen and a 3-month follow up period without treatment. At the end of the 4-month maintenance phase, 74.5% (38/51) of patients were clinically cured. However, the probability of remaining cured was just 34% 3 months after maintenance, and the median duration of remission was between 4 and 5 months (vs. 8.7 to 9 months in the Example). The rate of break through infections occurring during the maintenance phase was 25%. This is in stark contrast to the rate reported in the Example, which was less than half that, at 12%. Moreover, 59.3% of the women in the Comparative Example required antifungal therapy for VVC at some point during the study whereas none of the women in the case series had secondary yeast infections.[1]

[1] Note that some patients in the prospective portion of the Example were placed on prophylactic antifungal therapy, which precluded an accurate assessment of this complication.

The differences between the Example and the Comparative Example are remarkable, particularly considering that many of these patients were recruited as failures from the more rigorous controlled maintenance study of metronidazole vaginal gel. The relative contribution of boric acid and its mechanism of action in the Example remain unknown but lend clinical support to the in vitro discovery that boric acid has therapeutically relevant biofilm disrupting properties, which are enhanced with the addition of EDTA. The lack of complicating VVC noted in the Example likely relates to boric acid's antifungal activity and represents another important advantage of boric acid over currently approved BV therapies.

We claim:

1. A method for treating a vaginal infection and/or pathogenic vaginal biofilms comprising topically administering to a patient in need thereof a pharmaceutical composition consisting of: a) a therapeutically effective amount of boric acid in the absence of any therapeutic amount of acetic acid, b) optionally, one or more of a surfactant, a gelling agent, a buffer, a preservative, a detergent, an oil, an alcohol, an emulsifier, a solubilizer, a humectant, a bioadhesive, metronidazole, tinidazole, and a pharmaceutically acceptable carrier, wherein said vaginal infection is selected from the group consisting of bacterial infections, trichmoniasis, viral infections, and vaginal infections associated with urinary tract infections.

2. The method of claim 1 further comprising administering to said patient a bioactive agent selected from the group consisting of bergamot oil, tea tree oil or other essential oils, and zinc ion.

3. The method of claim 1 wherein the boric acid is topically applied to a vagina and/or a vulva.

4. The method of claim 1 wherein the boric acid is topically applied as an ointment, cream, gel, tablet, capsule, ovule, suppositories, solution, suspension, foam, film or liposomal composition or is contained within a vaginal ring, tampon, suppository, sponge, pillow, puff, or osmotic pump system.

5. The method of claim 1 further comprising administering to said patient a therapeutically effective amount of EDTA.

6. A method for treating and/or prophylaxis of a vaginal infection and/or pathogenic vaginal biofilms comprising topically administering to a patient in need thereof a composition comprising a therapeutically effective amount of boric acid and EDTA.

7. The method of claim 6 wherein said vaginal infection is selected from the group consisting of bacterial infections, vulvovaginal candidiasis, trichmoniasis, viral infections, and vaginal infections associated with urinary tract infections.

8. The method of claim 6 further comprising administering to said patient a bioactive agent selected from the group consisting of bergamot oil, tea tree oil or other essential oils, and zinc ion.

9. The method of claim 6 wherein the boric acid is topically applied to a vagina and/or a vulva.

10. The method of claim 7 wherein the amount of boric acid is at about its planktonic MIC value for the infection and the amount of EDTA is at about its planktonic MIC value for the infection.

11. The method of claim 1 further comprising administering to said patient an additional therapeutically active substance selected from the group consisting of metronidazole and tinidazole.

12. The method of claim 6 further comprising administering to said patient an additional therapeutically active substance selected from the group consisting of metronidazole and tinidazole.

13. A method for prophylaxis of a vaginal infection and/or pathogenic vaginal biofilms comprising topically administering to a patient in need thereof a pharmaceutical composition consisting of: a) a therapeutically effective amount of boric acid in the absence of any therapeutic amount of acetic acid, b) optionally, one or more of a surfactant, a gelling agent, a buffer, a preservative, a detergent, an oil, an alcohol, an emulsifier, a solubilizer, a humectant, a bioadhesive, metronidazole, tinidazole, and a pharmaceutically acceptable carrier, wherein said vaginal infection is selected from the group consisting of bacterial vaginosis and vaginal infections associated with urinary tract infections.

14. The method of claim 13 further comprising administering to said patient a bioactive agent selected from the group consisting of bergamot oil, tea tree oil or other essential oils, and zinc ion.

15. The method of claim 13 wherein the boric acid is topically applied to a vagina and/or a vulva.

16. The method of claim 13 wherein the boric acid is topically applied as an ointment, cream, gel, tablet, capsule, ovule, suppositories, solution, suspension, foam, film or liposomal composition or is contained within a vaginal ring, tampon, suppository, sponge, pillow, puff, or osmotic pump system.

17. The method of claim 13 further comprising administering to said patient a therapeutically effective amount of EDTA.

18. The method of claim 13 further comprising administering to said patient an additional therapeutically active substance selected from the group consisting of metronidazole and tinidazole.

* * * * *